(12) United States Patent
Burris et al.

(10) Patent No.: US 10,896,507 B2
(45) Date of Patent: Jan. 19, 2021

(54) TECHNIQUES OF DEFORMATION ANALYSIS FOR QUANTIFICATION OF VASCULAR ENLARGEMENT

(71) Applicant: THE REGENTS OF THE UNIVERSITY OF MICHIGAN, Ann Arbor, MI (US)

(72) Inventors: Nicholas S. Burris, Ann Arbor, MI (US); Brian D. Ross, Ann Arbor, MI (US); Benjamin A. Hoff, Ann Arbor, MI (US); Ella Kazerooni, Northville, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 58 days.

(21) Appl. No.: 16/138,121

(22) Filed: Sep. 21, 2018

(65) Prior Publication Data
US 2019/0087957 A1    Mar. 21, 2019

Related U.S. Application Data

(60) Provisional application No. 62/561,447, filed on Sep. 21, 2017.

(51) Int. Cl.
*G06K 9/00* (2006.01)
*G06T 7/00* (2017.01)
(Continued)

(52) U.S. Cl.
CPC .......... *G06T 7/0014* (2013.01); *A61B 5/0044* (2013.01); *A61B 5/02014* (2013.01);
(Continued)

(58) Field of Classification Search
CPC ... G06T 7/00; G06T 7/11; G06T 7/254; G06T 7/33; G06T 2207/30101;
(Continued)

(56) References Cited

U.S. PATENT DOCUMENTS

| 7,545,979 B2 * | 6/2009 | Fidrich | ..................... G06T 7/12 |
| | | | 382/128 |
| 8,233,681 B2 * | 7/2012 | Aylward | ................ A61B 90/36 |
| | | | 382/128 |

(Continued)

*Primary Examiner* — Mahendra R Patel
(74) *Attorney, Agent, or Firm* — Marshall, Gerstein & Borun LLP

(57) ABSTRACT

Thoracic aortic aneurysm is a common and lethal disease that requires regular imaging surveillance to determine timing of surgical repair and prevent major complications such as rupture. Current cross-sectional imaging surveillance techniques, largely based on computed tomography angiography (CTA) or magnetic resonance angiography (MRA), are focused on measurement of maximal aortic diameter, although this approach is limited to fixed anatomic positions and is prone to significant measurement error. The present techniques demonstrate novel approaches (generally termed herein "Vascular Deformation Mapping (VDM)") for assessing changes in aortic dimensions. The present techniques quantify three-dimensional changes in the anatomic dimensions of a vessel through a process that involves non-rigid co-registration of serial imaging data and quantification of vascular deformation on a 3D surface model using some derivation of the spatial deformations resulting from the optimized spatial transform.

20 Claims, 13 Drawing Sheets
(11 of 13 Drawing Sheet(s) Filed in Color)

(51) Int. Cl.

| | | |
|---|---|---|
| *G06T 7/254* | (2017.01) | |
| *G06T 7/33* | (2017.01) | |
| *A61B 5/00* | (2006.01) | |
| *G06T 7/11* | (2017.01) | |
| *A61B 5/02* | (2006.01) | |
| *A61B 6/00* | (2006.01) | |
| *G06T 19/20* | (2011.01) | |
| *G16H 50/50* | (2018.01) | |
| *G06T 7/35* | (2017.01) | |
| *G06T 19/00* | (2011.01) | |
| *A61B 6/03* | (2006.01) | |
| *A61B 5/055* | (2006.01) | |
| *G16H 30/20* | (2018.01) | |
| *A61B 5/0402* | (2006.01) | |

(52) U.S. Cl.
CPC .............. *A61B 6/032* (2013.01); *A61B 6/463* (2013.01); *A61B 6/466* (2013.01); *A61B 6/503* (2013.01); *A61B 6/504* (2013.01); *A61B 6/5205* (2013.01); *A61B 6/5288* (2013.01); *G06T 7/0016* (2013.01); *G06T 7/11* (2017.01); *G06T 7/254* (2017.01); *G06T 7/344* (2017.01); *G06T 7/35* (2017.01); *G06T 19/00* (2013.01); *G06T 19/20* (2013.01); *G16H 50/50* (2018.01); *A61B 5/0402* (2013.01); *A61B 5/055* (2013.01); *A61B 6/5217* (2013.01); *A61B 6/5258* (2013.01); *A61B 2576/023* (2013.01); *G01N 2800/329* (2013.01); *G06T 2200/24* (2013.01); *G06T 2207/10072* (2013.01); *G06T 2207/10081* (2013.01); *G06T 2207/10088* (2013.01); *G06T 2207/30101* (2013.01); *G06T 2210/41* (2013.01); *G06T 2219/2012* (2013.01); *G16H 30/20* (2018.01)

(58) Field of Classification Search
CPC ...... G06T 2207/10081; A61B 5/02014; A61B 6/503; A61B 5/0044; A61B 6/5288; A61B 6/032; G06K 9/00; C08L 75/04; A61L 27/50; G16H 50/50
USPC .................................. 382/121; 1/1; 351/246
See application file for complete search history.

(56) References Cited

U.S. PATENT DOCUMENTS

| | | | |
|---|---|---|---|
| 10,176,408 B2* | 1/2019 | Paik | G06K 9/6296 |
| 10,537,277 B2* | 1/2020 | Wu | A61B 5/7435 |
| 2004/0223636 A1* | 11/2004 | Edic | G06T 7/0012 |
| | | | 382/131 |
| 2007/0019846 A1* | 1/2007 | Bullitt | G06T 7/0014 |
| | | | 382/128 |
| 2007/0297657 A1* | 12/2007 | Mattes | G06T 7/246 |
| | | | 382/128 |
| 2008/0123927 A1* | 5/2008 | Miga | G06T 7/344 |
| | | | 382/131 |
| 2009/0322749 A1* | 12/2009 | Kassab | G06T 7/0012 |
| | | | 345/424 |
| 2011/0026794 A1* | 2/2011 | Sundar | G06K 9/44 |
| | | | 382/131 |
| 2013/0004044 A1* | 1/2013 | Ross | G06T 7/136 |
| | | | 382/131 |
| 2013/0301008 A1* | 11/2013 | Srivastava | G01B 9/02083 |
| | | | 351/246 |
| 2015/0104090 A1* | 4/2015 | Hopfgartner | G06T 17/10 |
| | | | 382/131 |
| 2015/0335304 A1* | 11/2015 | Lavi | A61B 5/02007 |
| | | | 600/407 |
| 2015/0339847 A1* | 11/2015 | Benishti | A61B 6/466 |
| | | | 382/131 |
| 2019/0240377 A1* | 8/2019 | Min | G06T 7/62 |
| 2019/0254535 A1* | 8/2019 | Harmelin | A61B 5/0077 |

* cited by examiner

FIG. 12A
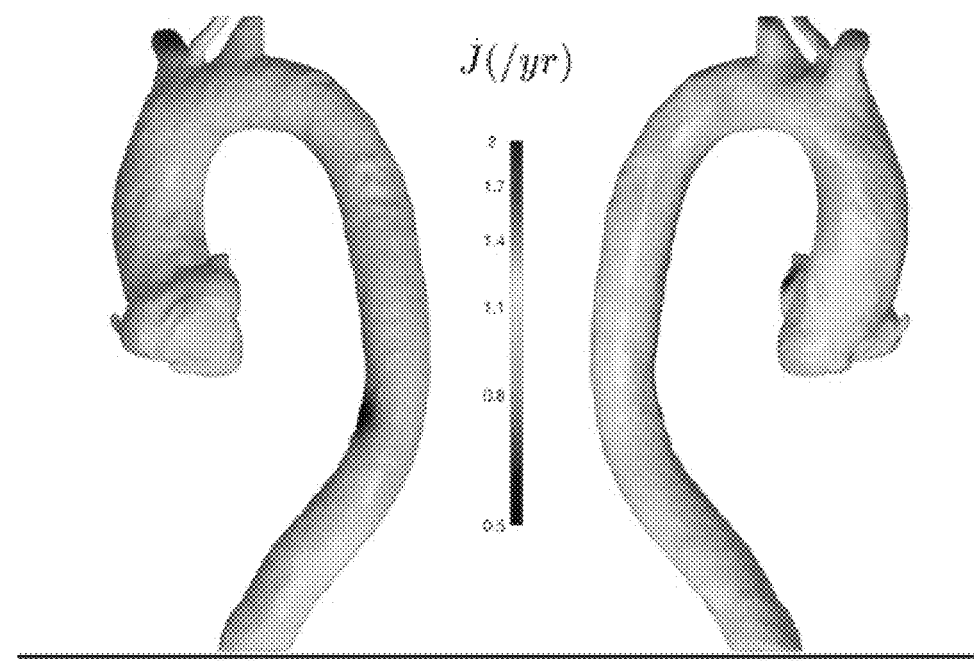
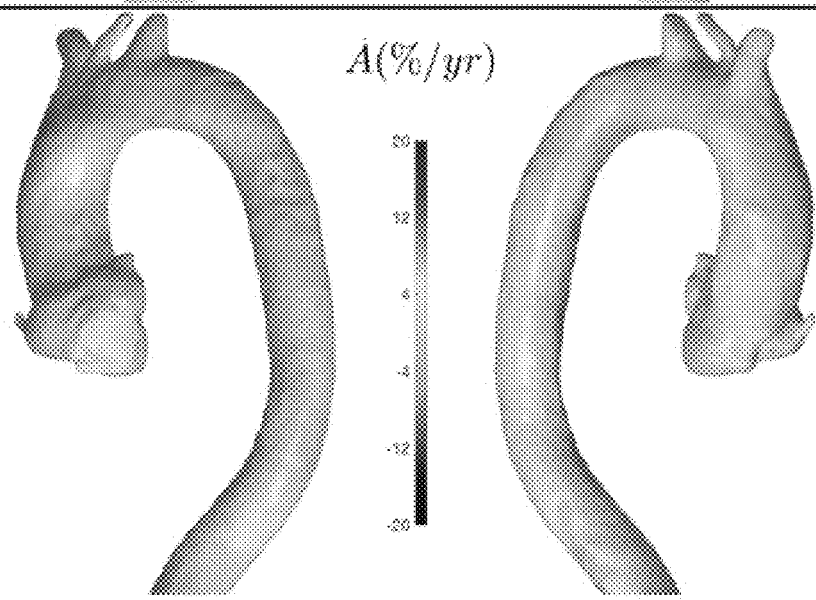
FIG. 12B

TECHNIQUES OF DEFORMATION ANALYSIS FOR QUANTIFICATION OF VASCULAR ENLARGEMENT

CROSS REFERENCE TO RELATED APPLICATIONS

The present application claims the benefit of U.S. Provisional Application No. 62/561,447, entitled "Techniques for assessment of spatial Jacobian for Quantification of Aortic Aneurysm Enlargement", filed on Sep. 21, 2017, which is hereby incorporated by reference herein in its entirety.

FIELD OF THE DISCLOSURE

The present disclosure relates generally to techniques for imaging analysis of aortic pathologies and, more particularly, to techniques for assessment of local anatomic deformation for quantifying aortic enlargement-based pathologies.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

The thoracic aorta is the largest blood vessel in the human body and subject to the most extreme hemodynamic forces. A healthy aorta is extremely durable, and able to absorb forces generated by the heart owing to its thick-walled and elastic nature. As a result of multiple factors (e.g., hypertension, atherosclerosis, genetic aortic syndromes, infection), the structural integrity and elasticity of the aortic wall can deteriorate, leading to progressive dilation of the aortic lumen and aortic aneurysm formation. Aortic dissection is a related form of aortic disease characterized by tearing of the inner layers of the aortic wall (i.e., intima and media), leading to the creation of a false lumen, or channel, within the aortic wall itself, which is structurally compromised and remains subjected to high pressures. This results in aneurysm formation in approximately 60% of patients with chronic aortic dissection of the descending thoracic aorta (Stanford type B)

The incidence of aortic aneurysm is increasing in the US population, and mildly dilated aortas are being incidentally detected at higher rates due to increased use of thoracic cross-sectional imaging for non-aortic indications (e.g., lung cancer screening). Recent data suggest that the prevalence of thoracic aortic dilation (>4 cm) is approximately 3% of individuals older than 55 years of age, which means that, based on current US population estimates, approximately 2.7 million people in the US would be recommended to undergo regular imaging of the thoracic aorta based on the current American Heart Association guidelines for imaging surveillance.

Imaging surveillance has a central role in the management of asymptomatic patients with aortic disease. The vast majority of patients with an aortic aneurysm, approximately 95%, are asymptomatic until they rupture, and only 40% of patients that rupture reach the hospital alive.

While the topic of aortic enlargement in abdominal aortic aneurysm (AAA) pre- and post-endovascular repair has been the focus of significant research effort, the natural history and mechanisms of thoracic aortic aneurysm (TAA) progression remain poorly understood, and only a handful of studies have attempted to measure growth rates of the thoracic aorta.

A major limitation in improving our understanding of TAAs is that the current clinical imaging surveillance techniques rely primarily on measurement of maximal aortic diameter. This parameter has been most widely studied and shown to correlate with future risk of aneurysm rupture. While the simplicity of diameter measurements is appealing, this approach is subject to a high degree of measurement error, in range of 2-5 mm despite optimal measurement technique. Error of this magnitude makes confident determination of aortic enlargement challenging considering that typical aortic growth rates are slow (e.g., 1 mm/year in the ascending aorta and 3 mm/year in the descending aorta), and this issue is further compounded when shorter follow-up intervals are analyzed (3 or 6 months) and when the aortic geometry is ovoid.

While several sections of the aorta are vertically oriented and can be viewed in cross-section on axial images, most of the aorta cannot be viewed in cross-section on standard image planes, requiring image-processing software to effectively straighten the aorta and allow true orthogonal diameter measurements to be made. The 2010 ACCF/AHA/AATS/ACR/ASA/SCA/SCAI/SIR/STS/SVM Guidelines for the Diagnosis and Management of Patients With Thoracic Aortic Disease was the first set of guidelines to raise this issue, and to recommend standard measurement locations in addition to measurement of maximal aortic diameter. Even with orthogonal measurements, the aorta is often not perfectly round in cross section, but rather ovoid or irregular, particularly in the setting of disease, further compounding the issue of exactly which diameter measurements to record and use for follow-up. Further, making aortic diameter measurements at pre-defined anatomic locations fails to capture interval growth at non-maximal locations, and does not detect the components of aortic enlargement in circumferential or longitudinal directions.

Height/weight-adjusted aortic area has been proposed as a better predictor of future rupture than maximal diameter, and several studies have investigated the use of volumetric measurements of TAA and AAA to improve the sensitivity for detecting aortic growth. However, similar to diameter measurements, aortic area and volumetric approaches must be performed at predetermined anatomic boundaries to ensure that measurements are comparable between studies, and small focal changes in aortic dimension may be camouflaged by a volumetric measurement approach. While area or volume measures may be more sensitive to detect overall growth of an aortic segment, information about localized change at a specific point along the aortic wall is not captured. Considering that surgical management recommendations are based on thresholds of size and growth rate, a diameter based measurement technique may lead to treatment recommendations that are either overly aggressive or conservative based on measurement error alone. Additionally, such size criteria used for surgical decision-making are based on historical measurement data and the resulting inaccuracies further emphasize the significant ongoing need for accurate and reproducible aortic measurements.

A significant need exists for a more sensitive and accurate method of measuring change in thoracic aortic dimensions, considering that accurate detection of small magnitude changes have important implications for improving understanding of aortic aneurysm progression and better informing treatment decisions.

SUMMARY OF THE INVENTION

The techniques include novel methods of applying quantitative deformation maps resulting from non-rigid serial image registration to detect and quantify enlargement of aortic dimensions.

In exemplary embodiments, the techniques include applying image segmentation software to high-resolution, volumetric imaging data, such as computed tomography angiography (CTA) or magnetic resonance angiography (MRA), to define a 3-dimentional model of the aorta. This process may be repeated on imaging data from a single patient acquired serially, e.g. from two unique temporally delineated scans (e.g., days, years) or from two unique phases in the cardiac-cycle within a single scan (i.e., systole, diastole). In exemplary embodiments, serial images are co-registered using a non-rigid transformation, e.g., b-spline warping, within the neighborhood of the defined segmentation. In exemplary embodiments, the degree of deformation resulting from the co-registration transformation is quantified locally on the defined segmentation surface, e.g., using either some derivation using the spatial Jacobian or direct quantification of triangulated surface area change. Changes in aortic dimensions can then be quantified after transformation of this data into a scale of millimeters (mm).

The present techniques address the problem of significant measurement error and variation that limit current clinical techniques of determining aortic enlargement, such as techniques that rely on measurement of maximal aortic diameter. Maximal aortic diameter is subject to significant error (up to ±5 mm). Additionally, standard maximal aortic diameter measurement techniques are limited in their ability to depict eccentric aortic enlargement and the gradation of enlargement along the length of the aorta. The present techniques, based on non-rigid deformation analysis, avoid such errors, as we show. Moreover, the present techniques further differ from existing techniques and commercial software in that the present techniques embed a multiple time point imaging assessment, e.g., measuring aortic enlargement between two separate time points, whereas conventional commercial software only offers methods to evaluate the geometry of the thoracic aorta at one time point.

In some examples, a method of quantifying enlargement of vascular dimensions comprises: obtaining a first volumetric imaging data for at least a segment of a vessel and determining a first 3-dimentional (3D) segmentation and model of the at least a segment of the vessel; obtaining a second volumetric imaging data for the segment of the vessel; registering the second volumetric imaging data to the first volumetric imaging data and determining a degree of deformation resulting from the registration; calculating a quantitative deformation metric using an optimized non-rigid transformation between the second volumetric imaging data and the first volumetric imaging data; and mapping of the quantitative deformation metric to vertices of a 3D vessel surface model for display.

In some examples, the degree of change in the at least a segment of the aorta is output to computerized display and/or to 3D printer for printing a 3D model for review by a care professional.

In some example, calculating the quantitative deformation metric includes calculating the degree of local deformation rate on the 3D surface model either using some derivation of the spatial Jacobian or direct calculation of triangulated surface area change resulting from the transformation relative to the characteristic difference between image data sets (i.e. time or arterial pressure).

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

This patent or application file contains at least one drawing executed in color. Copies of this patent or patent application publication with color drawing(s) will be provided by the United States Patent and Trademark Office upon request and payment of the necessary fee.

FIGS. 12A and 12B illustrates a comparison of VDM results using plots of Jacobian determinant versus isosurface mesh-based technique in a 60 year old patient with mildly dilated aortic root, but stable aortic dimensions by diameter and circumference measurements over a 3 years period. The Jacobian determinant technique demonstrates areas of apparent low-level aortic expansion at the mid ascending aorta and a focal area of compression at the mid-descending level (FIG. 12A); however, when the VDM analysis was performed using the isosurface mesh-based technique using the same image data and segmentation/registration, the results demonstrated decreased level of expansion at the ascending aorta compared to the Jacobain determinant technique and there the area of focal compression at the mid-descending aorta was no longer present (FIG. 12B).

DETAILED DESCRIPTION

Figure 1:
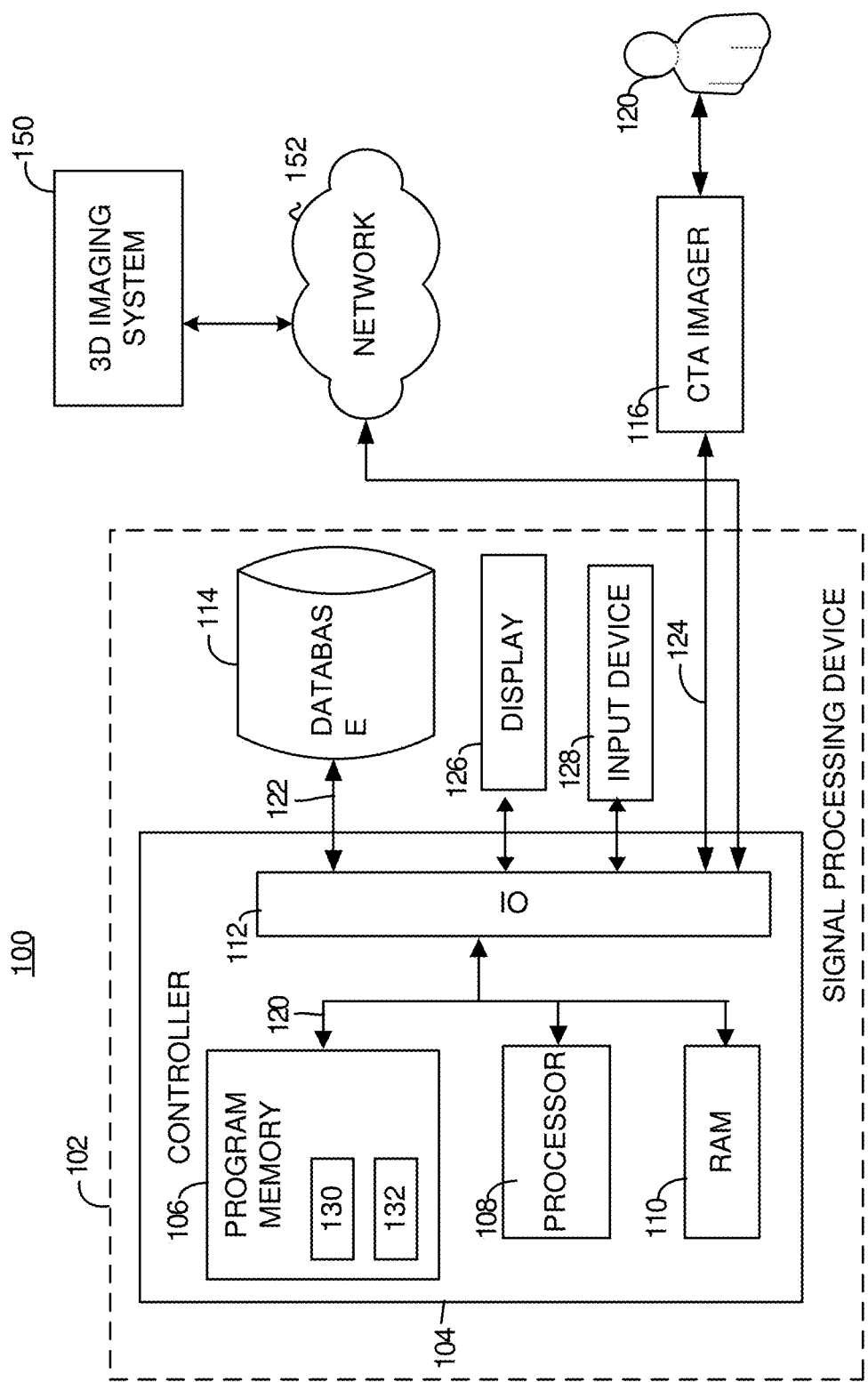
FIG. 1 is a schematic diagram of an example system for using an image deformation analysis to detect and quantify enlargement of aortic dimensions, in accordance with an example.

Thoracic aortic aneurysm is a common and lethal disease that requires regular imaging surveillance to determine timing of surgical repair and prevent major complications such as rupture. Current cross-sectional imaging surveillance techniques, largely based on computed tomography angiography (CTA), are focused on measurement of maximal aortic diameter, although this approach is limited to fixed anatomic positions and is prone to significant measurement error.

The present application provides techniques for assessing change in aortic dimensions using Vascular Deformation Mapping (VDM). In some embodiments, the techniques allow for quantification of three-dimensional changes in the aortic wall geometry through a process that involves non-rigid co-registration of serial volumetric imaging data, such as CTA or magnetic resonance angiography (MRA), and analysis of local aortic deformation derived from the optimized transformation. As we demonstrate, the present techniques may be utilized to measure change in the aortic wall geometry among patients with stable and enlarging thoracic aortic aneurysm and dissection. Furthermore, the present techniques yield diagnostic observations about the presence, distribution, and rate of aortic wall deformation that are not apparent by routine clinical evaluation. Further still, the present techniques allow for superposing patient-specific VDM results on a three-dimensional aortic model using color 3D-printing.

In various embodiments, the present techniques use novel application of spatial deformation metrics (i.e. derivations of the spatial Jacobian or change in model surface area) to quantify deformation of the aortic wall, e.g., by optimizing non-rigid image transformations to match high-resolution thoracic (electrocardiogram) ECG-gated imaging data (i.e. computed tomography angiography (CTA) or magnetic resonance angiography (MRA) acquired at varying intervals (i.e. time or cardiac phase). Spatial Jacobian matrices in this context describe the relative local distortion at each point in the image resulting from the automated image-based registration.

While non-rigid image warping co-registration techniques have been broadly utilized in diseases of the lungs and brain, no prior techniques have attempted or quantified deformation maps to assess interval aortic enlargement. Image intensity-based registration techniques have been reported to have sub-millimeter precision in many applications, which also translates to accuracy in the calculation of the resulting deformation metrics with well-optimized workflows. Quantitative assessment of registration accuracy is not straight forward, with many potential sources of error and a large number of degrees of freedom; however, as we have developed, the use of cost function penalties such as bending energy help to constrain and smooth deformation results while also maximizing anatomical feature alignment.

With the present techniques, deformation maps may be directly calculated from the optimized non-rigid transform, and are able to offer information about the local deformation of the aortic wall, including in vectorized components extracted from the full spatial Jacobian matrix (i.e. circumferential or longitudinal deformations) guided by centerline analysis, information that is not currently assessed by other techniques.

FIG. 1, described further below, illustrates an example block diagram of a system 100 illustrating the various components used in implementing an example embodiment of the present techniques. Example techniques that may be executed by the system 100 are provided in FIG. 2.

Figure 2:
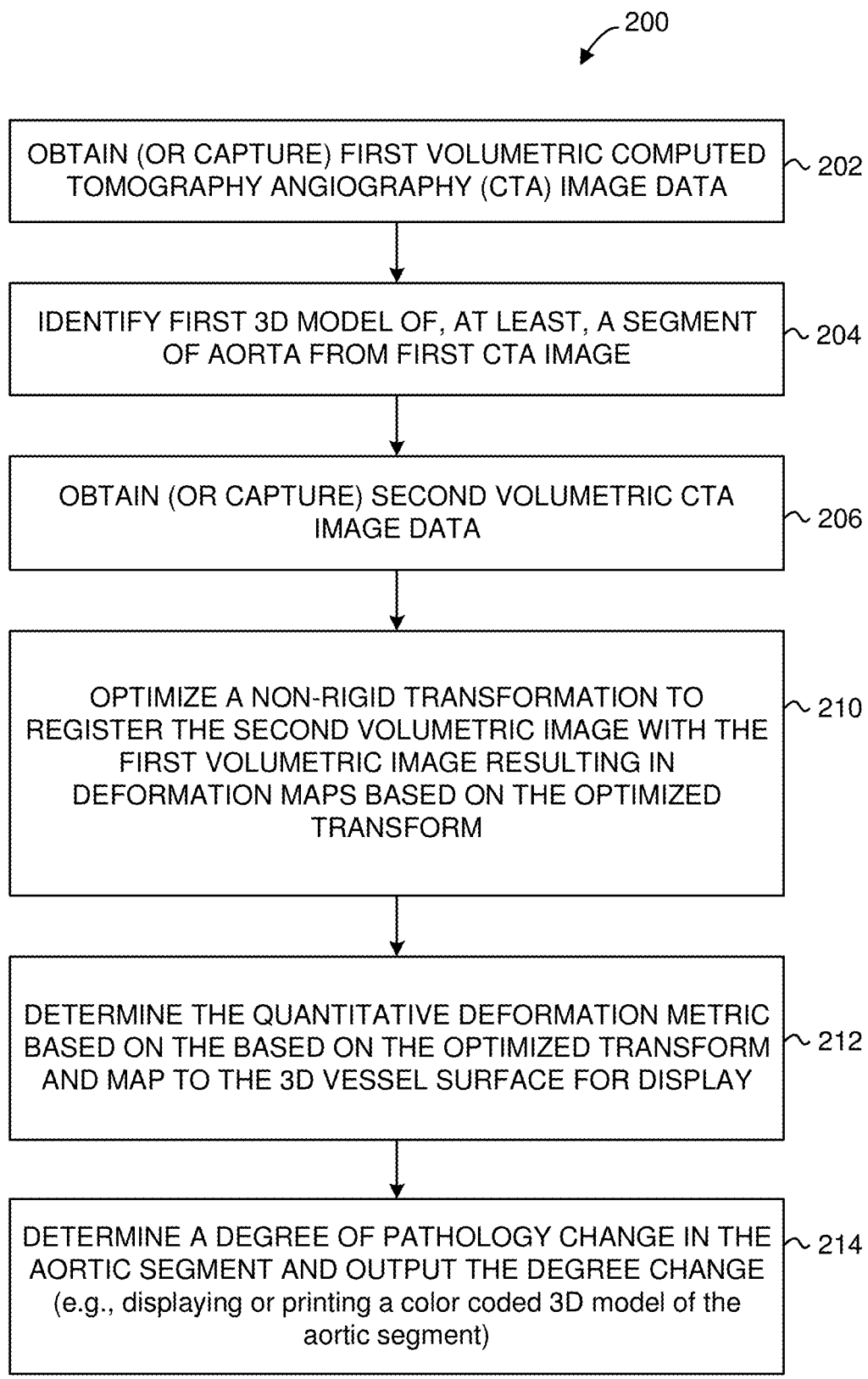
FIG. 2 illustrates an example process for using an image deformation analysis to detect and quantify enlargement of aortic dimensions that may be executed by the system of FIG. 1, in accordance with an example.

FIG. 2 illustrates an example process 200 for using a spatial Jacobian analysis to detect and quantify enlargement of aortic dimensions, in accordance with some embodiments herein. First, at a block 202, the system 100 (described further below) collects image data (such as CTA image data or MRA image data) from an imaging system and processes that image data to obtain first volumetric image data. In some examples the volumetric image data is provided directly from the imaging source, such as CTA imager or MRA imager. At a block 204, the system 100 identifies a first 3D model of, at least a segment of the aorta from this first volumetric image. At a block 206, the system 100 obtains (or captures) second volumetric image data. At a block 210, the system 100 optimizes a non-rigid transformation (such as by performing a b-spline warp) to register the second volumetric image data to the first volumetric image data resulting in an optimized spatial transform and corresponding displacement maps, which is then applied to the first 3D model of at least a segment of the aorta. At a block 212, the system 100 determines a spatial Jacobian determinant based on the displacement maps and interpolates the values onto the surface of the 3D model of at least a segment of the aorta. At a block 214, the system 100 determines a degree of pathology change in the aortic segment (e.g., changes in aortic wall dimensions) and outputs the degree change, e.g., displaying or printing a color-coded 3D model of the aortic segment.

The process 200 may include the additional processes described herein.

In some examples, the processes herein use an accurate 3D segmentation procedure in an automated or semi-automated measurement of aortic dimensions (e.g., maximal diameter, luminal area, segmental volume) at any point along the length of the aorta, for example. Given that maximal diameter remains the most commonly utilized parameter to predict the risk of future aortic complications and the need for surgical intervention, a computerized interface that allows users to easily visualize the overall maximal aortic diameter, or the maximal diameter within a specific segment of the aorta can be provided by the system 100, to allow clinicians to make decisions based on current diameter-based clinical guidelines, while at the same time utilizing the detailed VDM results herein to further refine the diagnostic understanding of a specific aortic pathology. In addition to automated detection of aortic diameter, in some examples, the processes herein measure luminal areas and volumes in an automated or semi-automated fashion, and further index to patient body size, allowing for a more sensitive change in overall aortic size than would be offered by diameter measurements alone. Additionally, the system 100 may provide a user interface to allow for visualization and interaction with the 3D model and various measurement parameters, providing a useful aid for the planning of endovascular stent grafting of the thoracic aorta, termed Thoracic Endovascular Aortic Repair (TEVAR), or endovascular stent grafting of the abdominal aorta, termed Endovascular Aneurysm Repair (EVAR). A critical step in planning TEVAR and EVAR is performing accurate measurements of the size and length of aorta immediately proximal and distal to the aneurysmal segment (i.e., the landing zone), so as to select the correct size of the endovascular prosthesis that prevents oversizing leading to potential aortic injury/rupture, or under sizing leading to potential endoleak. Once the automated 3D segmentation step is performed, such measurements can be easily made either in an automated fashion, or in a semi-automated fashion through computer software with user input. In addition to endovascular graft sizing based on aortic measurements at one time point, if volumetric imaging studies from two time points are available, VDM analysis can be performed and superimposed on the 3D aortic geometry to allow for determination of the stability of the aortic wall at a specific segment, which is potentially useful information for the purposes of procedural planning where the goal is to select a graft landing zone with maximal stability.

Empirical Examples

Study Population: Patients were identified through review of local picture archiving and communication system (PACS) archives, to identify adult (>18 years) patients with dilation of the thoracic aorta undergoing imaging surveillance, with at least two prior ECG-gated CTA or MRA examinations available for review. Patients were excluded if thoracic aortic enhancement was suboptimal (<250 HU) or there was significant motion/respiratory or other artifact affecting the thoracic aortic segments being clinically evaluated. After reviewing a total of 15 patients, several were excluded due to obvious pulsation artifact affecting the diseased aortic segment on CTA images (n=5), or low-resolution baseline CTA/MRA studies (slice thickness>1.5 mm for CTA, voxel size>1.5 mm for MRA) that were acquired at outside hospitals and uploaded to PACS system (n=4). One patient with type B aortic dissection was excluded from analysis due to difficulties with accurate segmentation of the false lumen due to poor enhancement related to slow flow and partial thrombosis. The aortic pathologies of those patients selected for analysis included ascending thoracic aortic dilation (n=1), descending thoracic aortic aneurysm (n=3), and thoracic aortic dissection (n=3).

Computed Tomography Angiography (CTA): CTA exams were performed on 64-detector CT scanners using helical acquisition mode (LightSpeed VCT or Discovery CT750HD, GE Healthcare, Waukesha, Wis., USA). Images were acquired through the entire thoracic aorta (lung apices to 2-cm below celiac artery) during intravenous injection of 95 mL iopamidol 370 mg 1/mL (Isovue 370, Bracco Diagnostics, Inc., Princeton, N.J., USA) at 4 mL/second, followed by a 100 ml saline chaser at 4 mL/second. Retrospective ECG-gating was used, with axial reconstructions at 0.625 mm slice thickness at 75% of the R-R cycle with ECG-modulated mA technique (20% of max mA) and 40% adaptive statistical iterative reconstruction (ASIR) for dose efficiency. Other scan parameters included: detector coverage—40 mm, DFOV 25 cm, gantry rotation time 0.4 seconds, tube current maximum 400-700 mA as determined by patient size, tube voltage—100-120 kVp.

Magnetic Resonance Angiography (MRA): a MRA test was performed on a 1.5 Tesla MRI scanner (Philips Medical Systems, Best, The Netherlands). Images were acquired covering the entire thoracic aorta using a three-dimensional, steady-state free-procession based non-contrast MRA with respiratory navigators and ECG-gating yielding high-resolution images of the thoracic aorta with isotropic spatial resolution of 0.8×0.8×0.8 mm-1.0×1.0×1.0 mm.

Image Segmentation: Segmentation of the aortic blood volume was accomplished with a user-defined threshold in contiguous regions followed by manual adjustments, performed using custom in-house algorithms developed in Matlab (Natick, Mass.) or commercially available software (Mimics; Materialize, Leuven, Belgium). Briefly, a threshold was chosen on a case-by-case basis to separate contrast-enhanced blood from the surrounding tissues and organs. Manual separation was required at the aortic valve and arch vessels. The surface structure was determined based on the segmentation mask and then subject to curvature flow smoothing.

Image Registration: Image registration was performed between sequential CTA/MRA studies using a custom Matlab interface to the Elastix open source software. Images were processed temporarily for registration with the following after manually cropping around the region of the aorta: (1) a 3D Wiener filter (3×3×3) was applied to limit the effects of noise, (2) Image values less than 0 HU were set to 0 HU to avoid lung position influencing the registration, and (3) the aortic blood segmentation mask was dilated by 6 mm to include aortic wall. Automated image registration included an affine optimization followed by a multi-resolution non-rigid b-spline warping optimization using mutual information (sub-sampled within the dilated segmentation mask) with bending energy penalty (set to 50). Three resolutions of b-spline grid spacing were used in descending order: 12, 6, and 3 mm. Total time for image registration was around 10 minutes on a standard high-end personal computer.

Vascular Deformation Mapping (VDM): Using the deformation fields generated from the final optimized non-rigid transformation, the spatial Jacobian tensor (F) and its determinant (J, characterizing volumetric distortion) are defined as all first-order derivatives at each voxel location:

$$F = I + \begin{bmatrix} \frac{\delta \Delta x}{\delta x} & \frac{\delta \Delta x}{\delta y} & \frac{\delta \Delta x}{\delta z} \\ \frac{\delta \Delta y}{\delta x} & \frac{\delta \Delta y}{\delta y} & \frac{\delta \Delta y}{\delta z} \\ \frac{\delta \Delta z}{\delta x} & \frac{\delta \Delta z}{\delta y} & \frac{\delta \Delta z}{\delta z} \end{bmatrix} \text{ and } J = |F|.$$

The spatial Jacobian tensor can further be projected onto a vector or plane of interest (i.e. along the circumference or length of the aorta) to determine a directional warping coefficient. Scaling of the Jacobian determinant for comparison between cases with varying interval amounts can be performed using the following equation:

$$\frac{d}{dt} J = J * tr\left(\frac{dF(t)}{dt} F^{-1}(t)\right).$$

Here, tr( ) denotes the trace, and t denotes the interval for normalization (i.e. time or pressure).

The normalized determinant of the 3D spatial Jacobian tensor, or simply referred to as the Jacobian determinant map, was calculated from the final optimized image transform and normalized by the time difference between imaging sessions using the above equation to indicate a deformation rate. Values of dJ/dt, also referred to herein as VDM values, were linearly interpolated to the vertex points of the 3D aortic model surface for display. Expansion between time points was visualized by greater values (red; dJ/dt>1), compression by dJ/dt<1 (blue), and no general deformation by dJ/dt=1 (green). Areas of expansion or compression were considered artificial if one of the following criteria was present: 1) visible motion artifact was present on source CTA images, 2) visible error was noted in image alignment after the image warping co-registration step, or 3) regions of expansion/compression were adjacent to the cut-planes of the 3D aortic segmentation (e.g., at level of the aortic valve or proximal arch vessels) as these areas are susceptible to minor differences in geometry resulting from manual segmentation.

Figure 3:
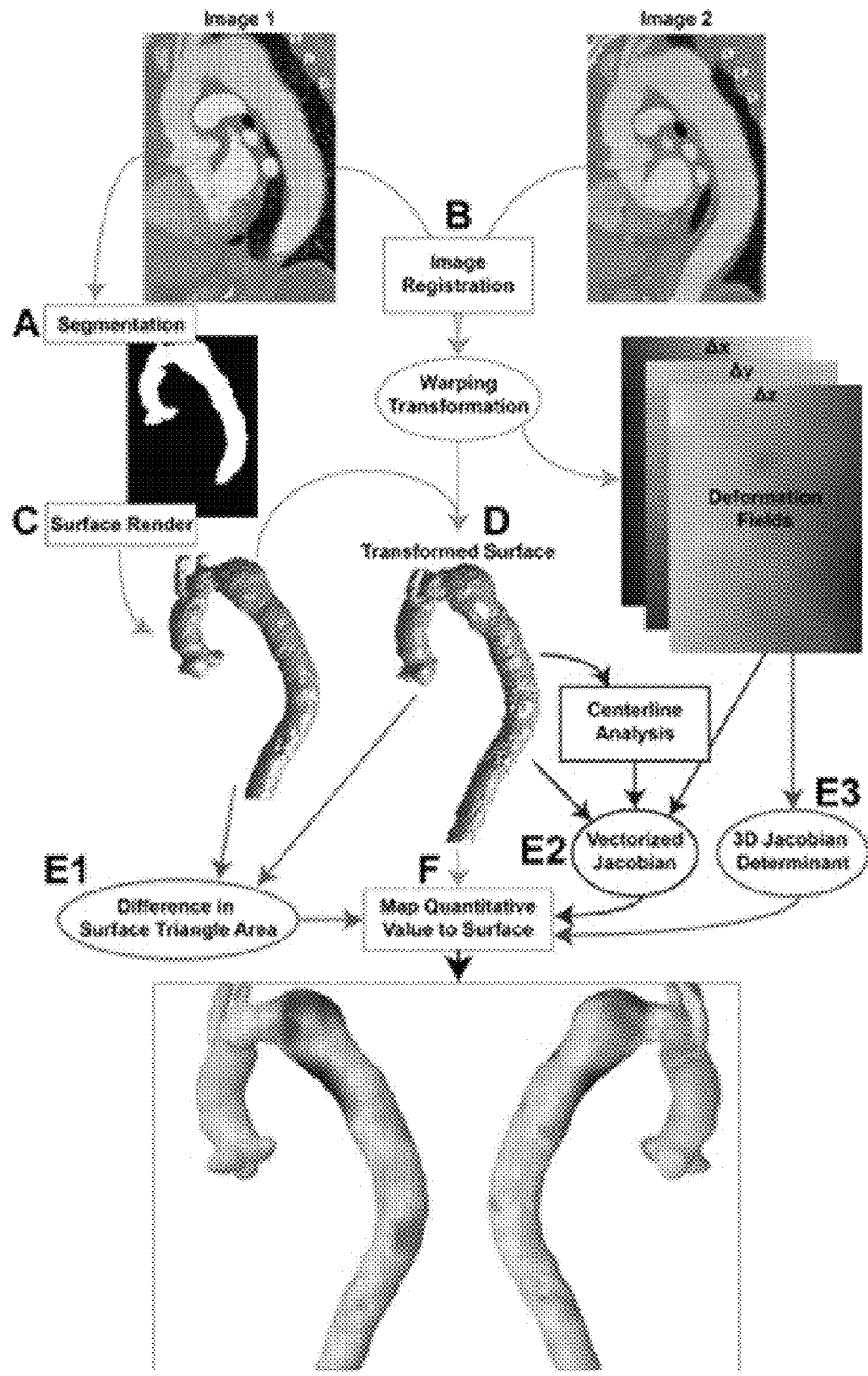
FIG. 3 illustrates Vascular Deformation Mapping workflow: Serial 3D images undergo digital image processing and analysis that involves process (A) segmentation of the contrast-enhancing aortic blood volume followed by process (B) non-rigid co-registration between image data within the neighborhood of the segmentation volume, resulting in an optimized warping transform and corresponding deformation fields. Process (C) 3D includes surface rendering of the binary segmentation volume is then generated and process (D) includes transformation using the optimized warping transform. Quantitative deformation metrics can then be calculated (e.g., using processes E1-E3) and mapped to the surface model process (F) for digital display or 3D printing.

A simplified workflow of this example implementation of the VDM technique is provided in FIG. 3. As shown, serial 3D images undergo digital image processing and analysis that involves a step (A) segmentation of the contrast-enhancing aortic blood volume followed by process and a step (B) non-rigid co-registration between image data within the neighborhood of the segmentation volume, resulting in an optimized warping transform and corresponding deformation fields. A step (C), a 3D surface rendering of the binary segmentation volume is generated. At a step (D) transformation using the optimized warping transform is performed. Quantitative deformation metrics may be calculated (e.g., using processes E1-E3) and mapped to the surface model process (step F) for digital display or 3D printing.

Alternatively, surface distortions on the 3D aortic model generated on the first image set may be directly quantified by calculation of the surface area for each triangulation of the 3D aorta surface model. The 3D aorta surface model obtained in step 204 of FIG. 2 is composed of a set of points defining the vertices of triangular faces. The surface area can then be calculated for each triangular face. Further, vertex points can then be transformed using the optimized non-rigid transform to the geometric frame of the second image data set. A change in surface calculated from each triangular facet can then be monitored and normalized by interval values to obtain a 2D planar deformation rate on the actual segmentation surface.

Figure 4:
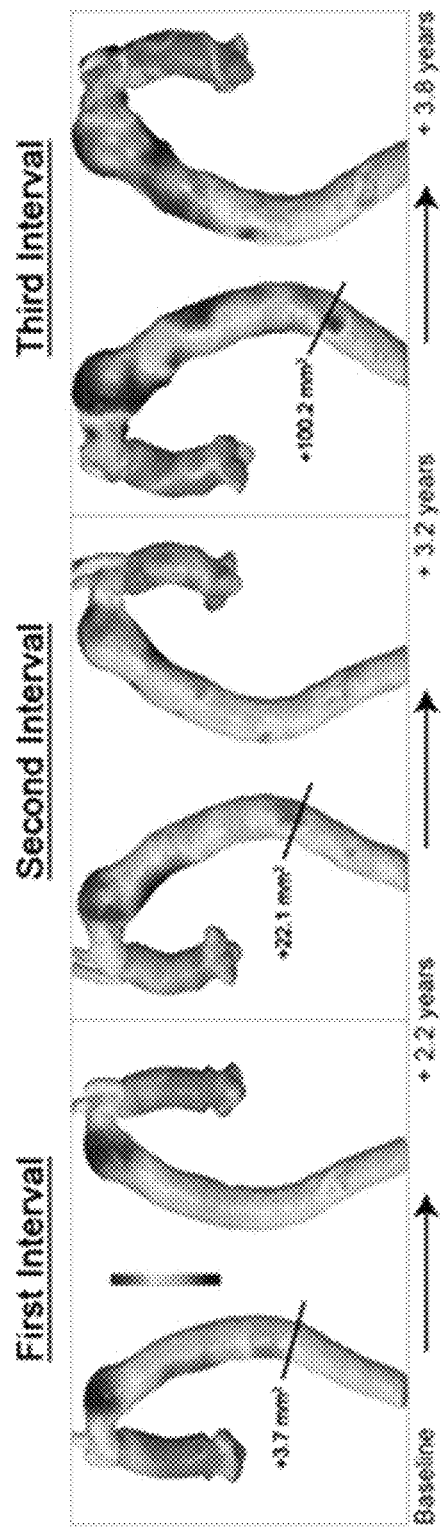
FIG. 4 illustrates progressive enlargement of an aortic aneurysm of the descending aorta in a 76-year-old patient with history of prior surgical repair of the ascending aorta. Aortic enlargement is noted at all intervals, but increases in rate and extent over time. Aortic lumen area ($mm^2$) measured at a single level (black line) in the distal descending aorta was used to corroborate a focal region of enlargement in the distal descending aorta seen on the Vascular Deformation Mapping (VDM) map. VDM values for replaced ascending aorta are not displayed due to artifact.

Evaluation of Aortic Aneurysm: The VDM analysis clearly depicted interval enlargement of the descending aortic dimensions in our first representative case of a 76 year-old female patient with a prior history of surgical repair of an ascending aortic aneurysm. The aortic arch and descending aorta were not included in initial surgical repair given the mild degree of pre-operative dilation; however, the distal arch and descending aorta were noted to progressively enlarge over three subsequent CTA examinations spanning a period of 3.8 years (FIG. 4). It is interesting to note that while the VDM shows enlargement of the proximal descending aorta at each interval, the extent and rate of enlargement progresses from the first interval to the last, consistent with the gradually accelerating and outwardly expanding nature of aortic enlargement described with aortic aneurysm. Additionally, while the clinical radiologist's assessment using maximal aortic diameters identified enlargement at each interval, the growth rate appeared to be decelerating by diameter measurements, and the growth was reported to be limited to the distal arch, whereas the VDM clearly highlighted more extensive enlargement along the length of the aorta, involving the proximal and mid-descending aorta at the second and third intervals. In an attempt to quantify and validate the VDM results, aortic area measurements were performed at a single level in the distal descending aorta with close attention paid to placing the measurement plane at precisely the same level and orientation on each study (FIG. 4). The luminal area measurements revealed a small increase in area at the first interval (3.7 mm$^2$), a larger increase in luminal area at the second interval (22.1 mm$^2$) and the greatest increase in luminal area at the third interval (100.2 mm$^2$) consistent with the accelerating growth visualized on the VDM map. For reference, an overall luminal increase of 100 mm$^2$ is approximately equal to a 1.1 mm increase in diameter assuming the lumen is circular.

Figure 5:
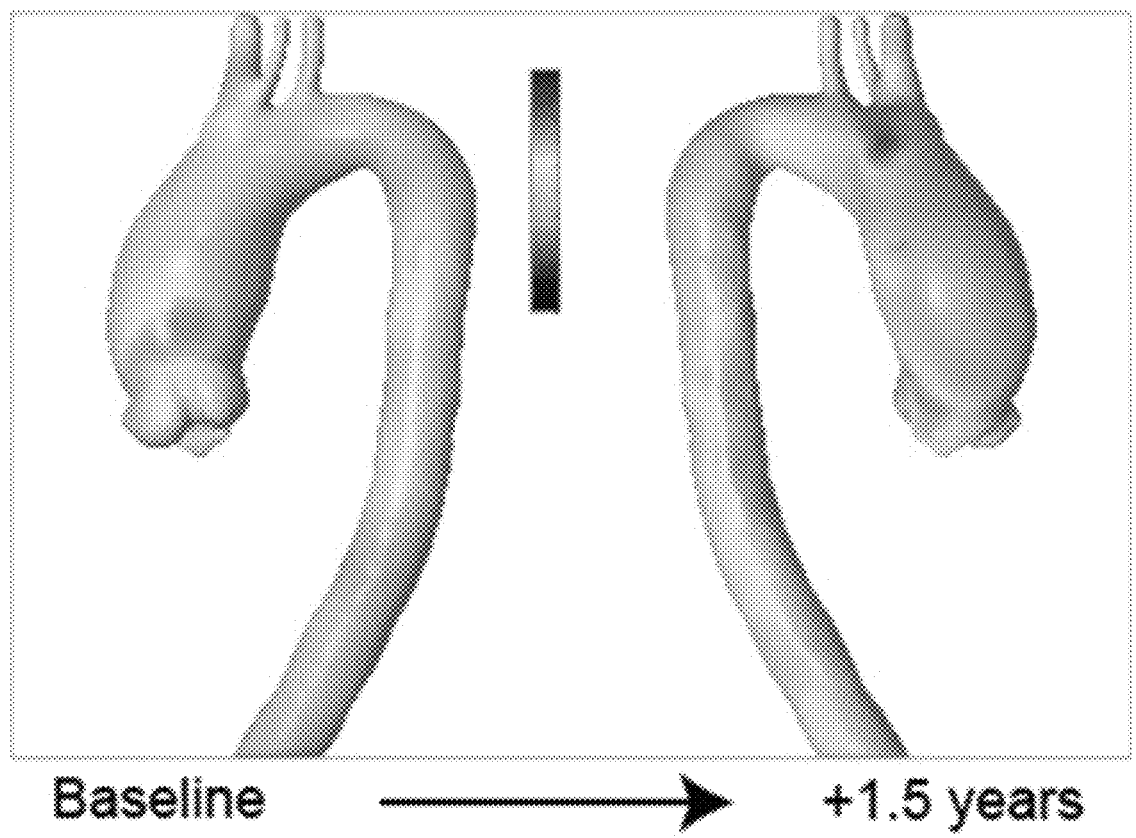
FIG. 5 illustrates a VDM analysis demonstrating no areas of high intensity wall expansion in a 66-year-old woman with a mild dilated ascending aorta (4.1 cm maximally). While aortic dimensions were stable by clinical diameter assessment, low-intensity areas of potential aortic enlargement were noted at the sinotubular junction and in the region of the innominate artery, suggesting the possibility of limited growth in these regions

In contrast to the above case, the VDM process was performed on a 66 year-old female patient undergoing imaging surveillance of a mildly dilated ascending aorta (maximally 4.1 cm at baseline), which revealed little deformation (FIG. 5). This case was selected for analysis to serve as a negative control, as no enlargement was detected by clinical diameter assessment, and enlargement of the ascending aorta is both significantly slower and less common than enlargement of the descending aorta, especially when the degree of dilation is mild. The VDM process did not reveal any areas of rapid growth in the ascending or descending aorta and the majority of the 3D surface area of the thoracic aorta showed |J| values close to 1 (green), compatible with stable aortic dimensions. However, several small regions of moderate deformation were detected, one at the level of the sinotubular junction, another in the proximal arch in the region of the origin of the innominate artery, and the last at the mid-descending level.

Figure 11A:
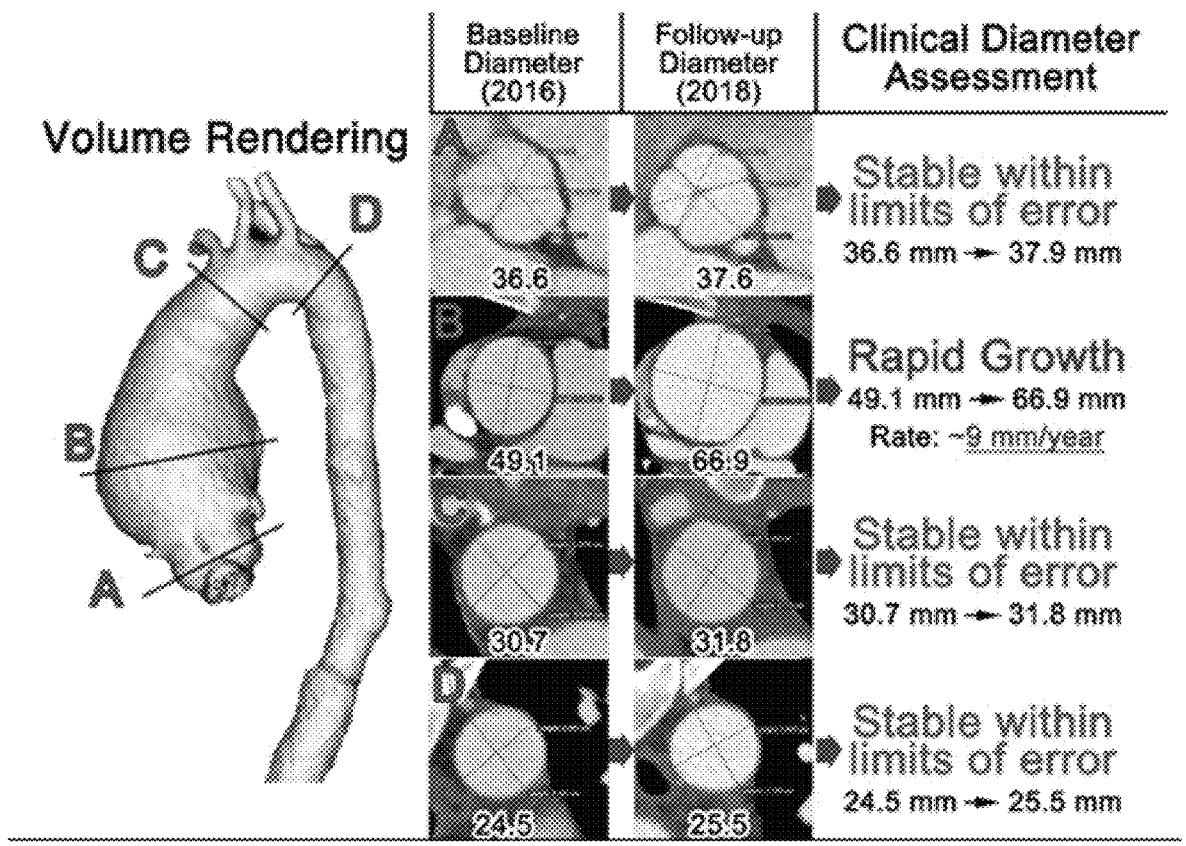
FIGS. 11A and 11B illustrate a comparison of diameter (FIG. 11A) vs. VDM (FIG. 11B) techniques for assessing growth of the thoracic aorta. Diameter and VDM techniques both detect rapid growth of the mid ascending aorta (location B). However, VDM identifies a gradation of slow growth extending from the ascending aorta into the arch (location C), and detects a region of slow growth in the descending aorta that was not suspected (location D). VDM clearly demonstrates that the right (RCA) and left (LM) coronary ostia arise from regions of growing aortic wall (purple arrows), informing surgical planning.
Figure 11B:
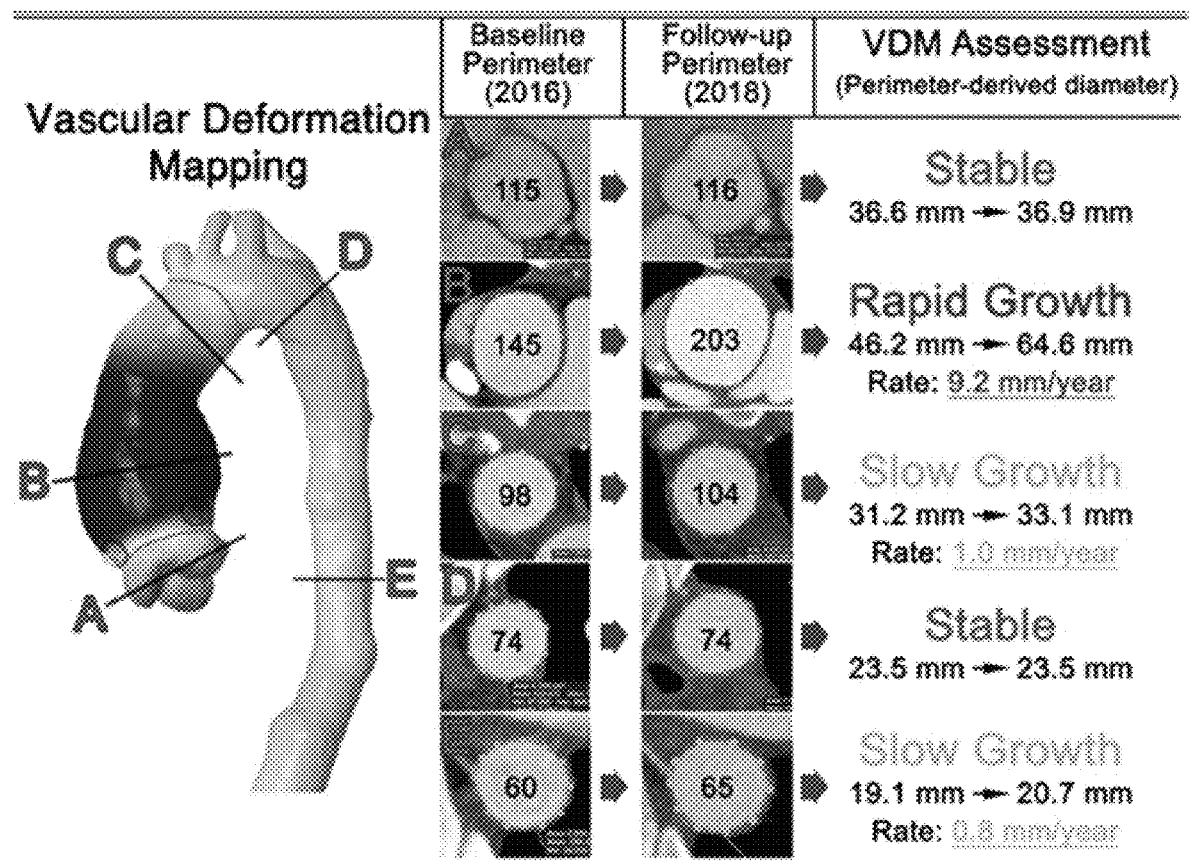

FIGS. 11A and 11B provides data for another example, specifically of a subject with aortitis and a rapidly enlarging ascending aortic aneurysm undergoing pre-surgical evaluation. While the tubular ascending aorta met size criteria for surgical repair, an accurate assessment of growth in adjacent segments was desired to determine the extent of repair (i.e., how much aorta to resect), as replacement of the aortic root and arch carry added technical challenges and patient risk. Maximal diameter measurements were performed on clinical CTA studies spanning a 2-year period (FIG. 11A). Rapid growth of the mid-ascending level was clearly detected by diameter measurements with a calculated growth rate of approximately 9 mm/year. Although there was approximately 1 mm of increase in the maximal aortic diameter at the level of the sinuses, proximal arch, and distal arch, the conclusion of clinical diameter assessment was that these segments were stable within the limits of measurement variability (i.e., ±2 mm). Subsequently, VDM analysis was performed on the same CTA studies (FIG. 11B) and results were validated by comparison with paired luminal circumference measurements.

In agreement with diameter measurements, rapid growth (9.2 mm/year) was noted at the ascending aorta by VDM analysis and the aortic root dimension were stable over the 2-year interval. VDM analysis demonstrated that growth of the ascending aorta extended proximally to involve the sinotubular junction, from which both the right and left coronary ostia arose, implying the need for coronary reimplantation. In disagreement with diameter assessment low intensity (1.0 mm/year), eccentric growth was noted at the proximal arch, with a higher degree of growth along the greater curvature (yellow arrow) than the lesser curvature (purple arrow). Lastly, an area of low intensity growth (0.8 mm/year) was detected in at the mid-descending level which was not clinically suspected but consistent with the patient's aortitis (blue arrowhead). Using VDM results, a surgical repair strategy was devised that maximized resection of diseased aortic tissue while balancing surgical risk (FIG. 11B, grey dotted line). Aortic growth occurs as a result of failing aortic wall structural integrity, however, diameter-based assessments are often limited for confident detection of slow growth due to measurement variability and do not depict growth in a three-dimensional manner.

FIGS. 12A and 12B provides data for a subject undergoing imaging surveillance of a mildly dilated aortic root (42 mm maximally at the sinuses) using magnetic resonance angiography. Two MRA studies were compared using the VDM analysis spanning a historical data collected for 3 year period, with the first study performed in 2015 and the follow-up study performed in 2018. Based on both standard clinical diameter measurements and paired luminal circumference measurements, there was no detectable change in the thoracic aortic dimensions. VDM analysis using Jacobian determinant technique demonstrated no areas of significant aortic deformation, but did show scattered low-level areas of mild expansion in the ascending aorta and a focal area of compression at the mid-descending aorta although there were no areas of high-level aortic expansion (FIG. 12A,). This case was also analyzed using the isosurface mesh-based technique, as described above and results showed similar scattered low-level areas of aortic expansion. However, the area of low-level expansion in the ascending and focal compression at the mid-descending aorta were less apparent using the isosurface mesh-based technique compared to the Jacobian determinant technique (FIG. 12B).

Figure 6:
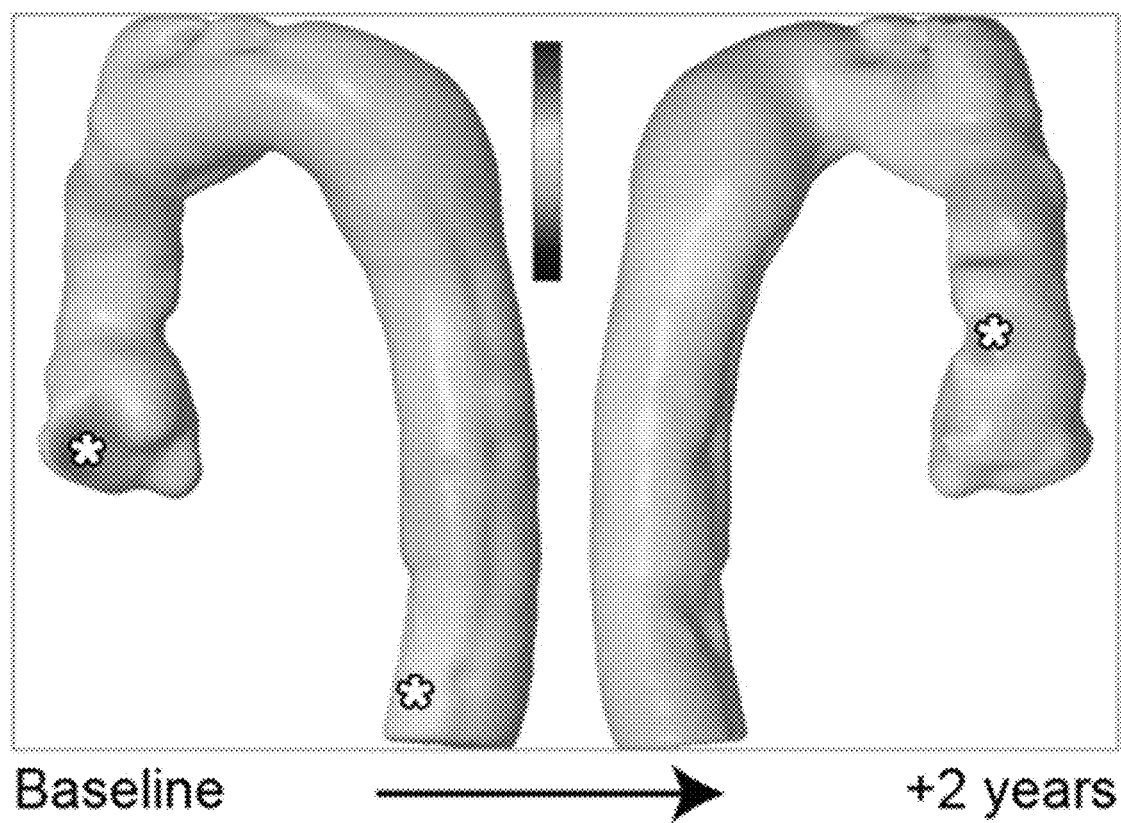
FIG. 6 illustrates overall stable aortic dimensions in a 56-year-old man with a history of surgical repair of the ascending aorta for type A dissection with residual dissection flap in the aortic arch and descending aorta. Small areas of apparent aortic expansion at the aortic root and distal descending aorta are likely due to mild co-registration artifact.

Evaluation of Aortic Dissection: Aortic dissection and aortic aneurysm are unique in their pathophysiology; however, the ultimate consequence of both pathologies is the same—dilation of the aortic wall due to weakened structural integrity. In both aneurysm and dissection, clinical surveillance guidelines and surgical decision-making are based on observation of the absolute aortic dimensions and the rate of aortic enlargement. As such, the VDM process can be used to monitor progression (i.e., enlargement) of aortic dissection patients. In the first representative case, we present the results of a 56-year-old patient with a prior history of surgically repaired dissection of the ascending aorta, with a residual dissection flap involving the native aortic arch and descending aorta (FIG. 6). The VDM process showed values close to 1 (green) throughout the majority of the aorta, compatible with stable dimensions of the true and false lumen during the 2-year time interval, in agreement with the clinical diameter assessment. There were several small areas of apparent mild enlargement in the ascending aorta and the distal descending aorta, which are thought to be due to imprecisions in co-registration caused by slight differences in cardiac and respiratory phase between studies, resulting in minor differences in aortic angulation (i.e., "bending"), although no definite misregistration was visually apparent.

Figure 7:
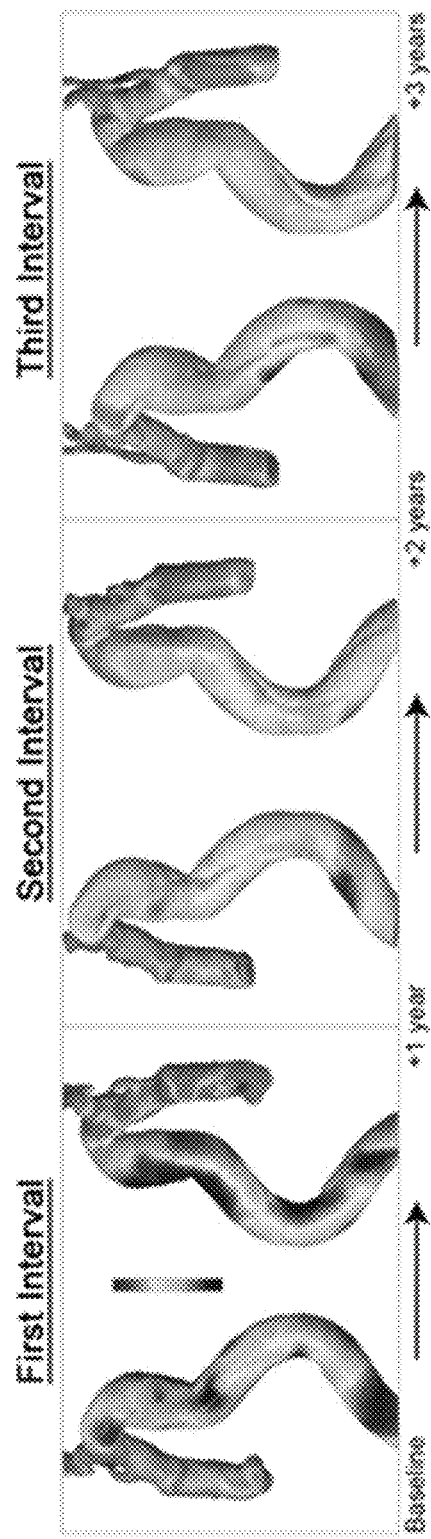
FIG. 7 illustrates progressively enlarging aortic dimensions in 76-year-old man with a history of type B aortic dissection over 3 intervals with the rate of enlargement noted to progressively decrease during follow up. The highest intensity regions of enlargement were at the level of the proximal and distal descending aorta levels corresponding to the location of entry tears in the dissection flap. Clinical diameter assessment detected a 4 mm interval growth at the second interval in the distal arch, but no definite enlargement was noted at the first or third intervals. VDM values for surgically replaced ascending aorta are not displayed due to artifact.

In contrast, FIG. 7 illustrates a 52 year-old man with a history of type B aortic dissection who had 2 ECG-gated CTA studies available for analysis, the first approximately 1 year after the onset of his dissection and a follow-up study performed 6 months after the first. Based on the clinical report, there was suspicion for approximately 1-2 mm of interval enlargement of the distal aortic arch, but the conclusion of the clinical assessment was that there had been no definite enlargement, as the observed change in diameter was within the range of measurement error. The VDM process, in this example, demonstrated nearly diffuse enlargement of the false lumen throughout the distal aortic arch and descending aorta, with a corresponding decrease in size of the true lumen, changes that are frequently observed in chronic aortic dissection. It is important to note that while the absolute change in maximal aortic dimension was thought to be small (1-2 mm), the rate of growth is noted to be significant due to the short interval (6 month) between the two studies. This ability to detect growth over short intervals is particularly useful in the setting of patients with recent aortic dissection, as there is a proven clinical benefit to endovascular (TEVAR) repair in the subacute period (2 weeks-3 months post-dissection). Of note, there was visually apparent motion artifact in the ascending aorta on CTA images leading to difficulty with image co-registration, which is manifested on the VDM as a wavy aortic wall contour and areas of high and low Jacobian determinant (red and blue, respectively) on adjacent areas of the aortic wall.

Figure 8:
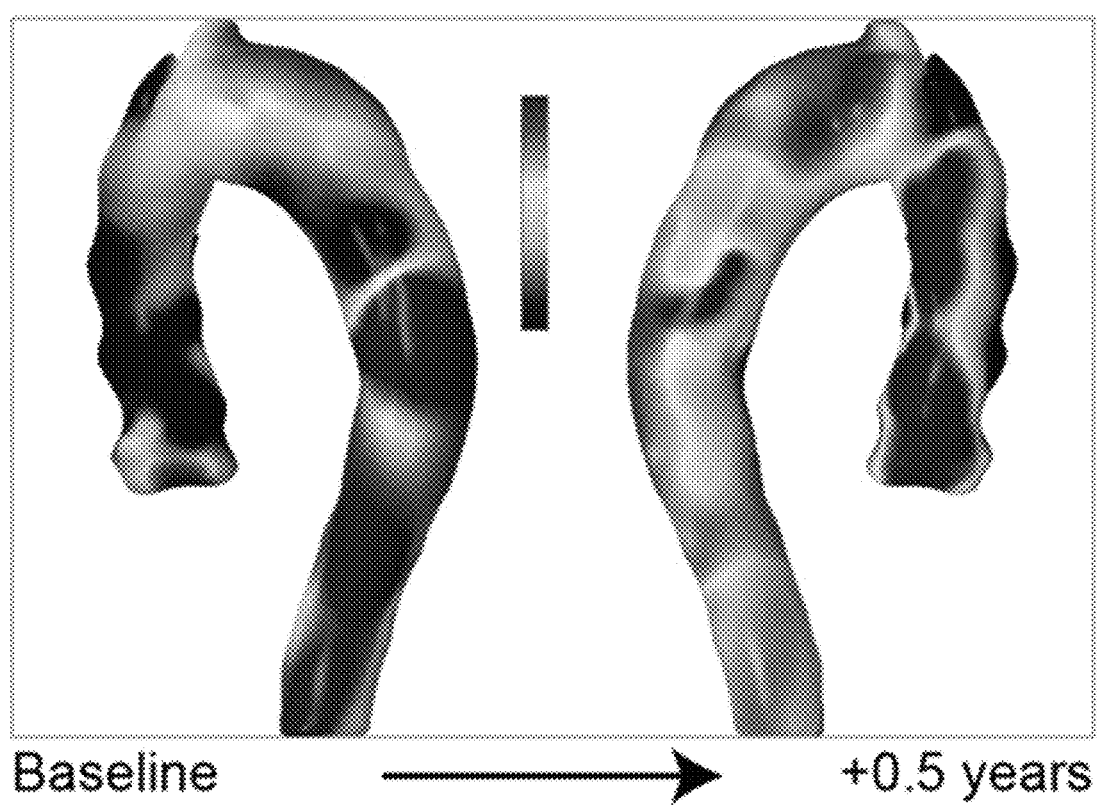
FIG. 8 illustrates VDM analysis of a 52-year-old man with a history of type B dissection shows interval expansion of the false lumen (red) with interval compression of the true lumen (blue) over a short interval of 6 months. Clinical diameter measurements suggested 1-2 mm increase in maximal dimensions, but no definite enlargement was described as the diameter change was within the range of measurement error. Cardiac motion artifact in the ascending aorta results in a wavy aortic wall contour and areas of high and low VDM values on opposite sides of the aortic wall.

FIG. 8 illustrates a VDM process for a 76-year-old man with a history of ascending aorta replacement, who developed a type B aortic dissection on the baseline study and had 4 surveillance CTAs performed over a 3-year period available for analysis. Comparing the clinical reports of the first and most recent CTA studies, the patient experienced up to 6 mm of enlargement overall at various points along the descending aorta during the 4-year follow-up period; however, using clinical diameter measurements interval enlargement was only confidently detected at the second interval. During the first interval, the VDM analysis revealed several areas of enlargement along the descending aorta, with the most intense areas in the proximal and distal descending aorta characterized by enlargement of the false lumen and compression of the true lumen. Despite the distal descending aorta being susceptible to image co-registration error related to respiratory variation, we did not visually detect any issues with image co-registration. On re-examination of the CTA studies, there was suggestion of 1-2 mm of aortic enlargement at these levels by diameter assessment. Furthermore, the entry tears that allow blood to flow from the true lumen into the false lumen were located at the proximal descending and distal descending levels, the locations of the most rapid growth, supporting the VDM results that enlargement had occurred in these regions. At the second interval the VDM map again demonstrated regions of false lumen enlargement; however, the rate of aortic enlargement was decreased. Lastly, during the third interval the descending aorta appeared to show only a small area of continued false lumen enlargement at the mid descending level, and otherwise no interval change. This observed gradual deceleration of aortic growth over time has been previously described in patients with chronic aortic dissection. While the mechanisms underlying the evolution of chronic type B dissection remain poorly understood, the wall of an acutely dissected aorta contains minimal fibrosis, and structural integrity of the wall is low. With increasing chronicity the aortic wall undergoes a process of adaptive remodeling, mainly through increased collagen deposition, leading to increased wall rigidity and a decreased rate of enlargement. Unfortunately, such remodeling processes are insufficient to prevent aneurysm formation in some patients who remain at risk for rupture. With the present techniques, however, the ability to accurately measure the rate of aortic enlargement at each follow-up interval may better inform clinical management through improved depiction of the overall growth trend (i.e., accelerating vs. decelerating), and may contribute to a better understanding of the natural history of aneurysm formation among patients with chronic aortic dissection.

Figure 9:
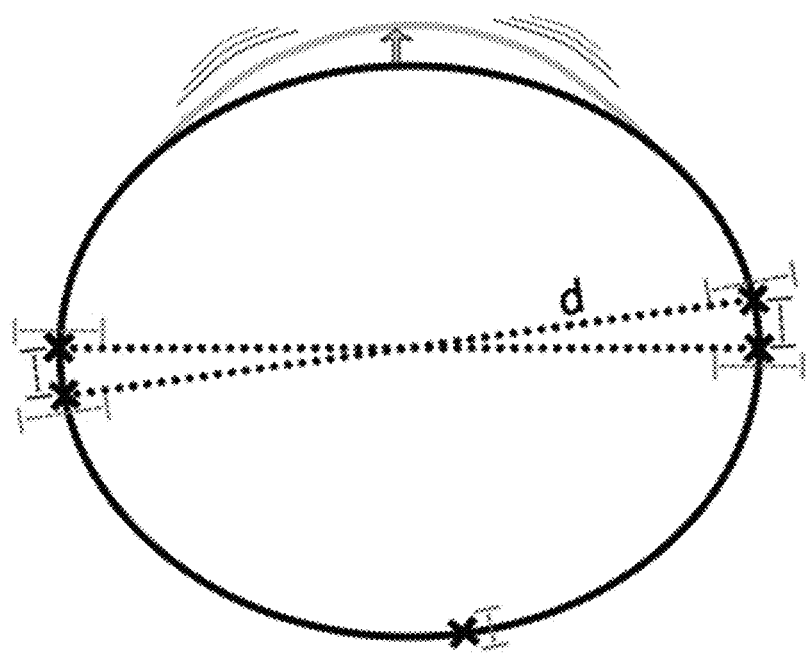
FIG. 9: Diagram of sources of measurement variability with maximal diameter and VDM measurement techniques. Variability in diameter measurements arises from three potential user-specific inputs: placement of the near-wall caliper (green error bar), placement of the far-wall caliper (red error bar) and sight differences in radial position of diameter measurement in non-circular aortic segments (blue error bar). The non-rigid image registration techniques employed in the VDM analysis are reported to have sub-millimeter precision (purple error bar), and allow for measurement of growth along the circumference and length of the aorta, making detection of local regions of non-maximal growth possible (grey area of wall bulging).

We believe that the early results presented here clearly demonstrate several unique advantages of the present techniques over maximal diameter measurements for assessment of aortic enlargement in the setting of aneurysm and dissection. First and most importantly, we believe that application of the present techniques can result in reduced measurement error, as it employs the full 3D image data along the entire length of the aorta, rather than diameters placed at fixed locations along the aortic length. Furthermore, our approach relies on modern semi-automated non-rigid image registration techniques that can align CTA images with a precision in the range of 0.5-1 mm. The reported 2-5 mm rage of error associated with aortic diameter measurement on CTA or MRA arises from several potential sources, including variability in placement of the measurement calipers along the near and far wall, as well as variability in the rotation of the diameter plane when the aorta is not uniformly circular as shown in FIG. 9. However, in various examples, the present techniques rely on modern non-rigid image co-registration techniques that are able to match each location along the 3D aortic wall surface with sub-millimeter accuracy.

Further, the present techniques offer the distinct advantage of being able to map a continuous range of growth rates in a 3D fashion, both along the entire length of the aorta and around its circumference, whereas aortic diameter measurements are limited to a single radial position at a fixed anatomic location. Additionally, wall deformation can be assigned vectors, allowing for measurement of directional deformation in addition to overall magnitude, a characteristic of aortic aneurysm growth that has not been previously quantified in situ. Separating the full Jacobian tensor into components of normal, circumferential tangent, and longitudinal tangent magnitudes may provide an even more nuanced understanding of changes in aortic wall geometry. Volumetric and cross-sectional area/circumference measurements, while reported to be more sensitive for aortic enlargement, rely on discreet predefined anatomic boundaries of aorta (i.e., start and stop points along the length of the aorta), and are therefore limited in determining the spatial location and gradation of aortic enlargement. The three-dimensional nature of VDM lends itself to robust and easily interpretable data visualization modalities that are customizable and approachable for surgeons, and other non-imager aortic specialists. Furthermore, physical models displaying VDM may now be easily and economically 3D printed and provided to surgeons pre-operatively to aid in surgical planning. While surgical decision-making remains a complex and patient-specific task, mapping the distribution of growth along the entire thoracic aorta, especially areas of growth at non-maximal locations, allows for the possibility of tailoring the surgical repair technique to include areas of slow growth that may not otherwise be detected by diameter measurements, and could potentially necessitate future re-operation.

Further still, as a result of the spatially continuous and quantitative nature of the present techniques, the present techniques reduce measurement error, increase sensitivity for detection of eccentric growth, and they make small magnitude aortic enlargement analysis possible. The rate of aortic enlargement, rather than absolute increase in maximal diameter, can be easily calculated and visualized. The rate of aortic enlargement is more closely related to the underlying structural and cellular mechanisms that drive aneurysm progression, and is likely a better indicator of risk among patients with aortic aneurysm. Unfortunately, the rate of enlargement often cannot be accurately calculated from aortic diameter measurements due to significant measurement error, especially when time intervals—the denominator in a rate measurement—are short. The decreased measurement error attainable with the present techniques may allow confident determination of slow aortic enlargement over short time intervals (e.g., 3-6 months), rather than the several year time-frame often required for diameter measurements. Earlier detection and more accurate quantification of aortic growth may allow for more targeted and aggressive treatment of aortic disease, better informed decisions to undergo major aortic surgical or endovascular procedures, and may be useful in the research setting where aortic enlargement is an outcome of interest and follow-up periods are limited by cost or other logistical considerations. Furthermore, the frequency of surveillance imaging can be better tailored to an individual if the stability of their aorta can be more accurately assessed; patients with slow growing or stable aneurysms can have imaging spaced to 2-3 year intervals, allowing for more efficient healthcare utilization, whereas patients with rapid enlargement can undergo imaging more frequently in hopes of minimizing the incidence of potentially predictable and preventable complications.

In FIG. 1, the system 100 includes a signal-processing device 102 (or "signal processor" or "diagnostic device") configured to collect CTA image data taken from a patient 120 via a CTA imaging device 116 in accordance with executing the functions of the disclosed embodiments. The signal-processing device 102 may have a controller 104 operatively connected to a database 114 via a link 122 connected to an input/output (I/O) circuit 112. It should be noted that, while not shown, additional databases may be linked to the controller 104 in a known manner. The controller 104 includes a program memory 106, one or more processors 108 (may be called microcontrollers or a microprocessors), a random-access memory (RAM) 110, and the input/output (I/O) circuit 112, all of which are interconnected via an address/data bus 120. It should be appreciated that although only one processor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124, which may include one or more wired and/or wireless (Bluetooth, WLAN, etc.) connections, may operatively connect the controller 104 to the imaging device 116 through the I/O circuit 112. In other examples, the imaging device 116 may be part of the signal-processing device 102.

The program memory 106 and/or the RAM 110 may store various applications (i.e., machine readable instructions) for execution by the processor 108. For example, an operating system 130 may generally control the operation of the signal-processing device 102 and provide a user interface to the signal-processing device 102 to implement data processing operations. The program memory 106 and/or the RAM 110 may also store a variety of subroutines 132 for accessing specific functions of the signal-processing device 102. By way of example, and without limitation, the subroutines 132 may include, among other things: a subroutine for collecting volumetric image data from the imaging device 116, a subroutine for pre-processing that image data, a subroutine for obtaining (or capture) first volumetric image data, a subroutine for identifying first 3D model of, at least, a segment of aorta from first image, a subroutine for obtaining (or capture) second volumetric image data, a subroutine for optimizing b-spline warp to register second volumetric image to first volumetric image and for determining degree of deformation from resulting optimized transformation, a subroutine for determining spatial Jacobian rate or surface area rate of change on the surface of the 3D model of, at least, a segment of aorta, and subroutines for determining a degree of pathology change in the aortic segment (e.g., changes in anatomic dimensions) and for outputting the degree change, e.g., displaying or printing a color coded 3D model of the aortic segment.

The subroutines 132 may also include other subroutines, for example, implementing software keyboard functionality, interfacing with other hardware in the signal processing device 102, etc. The program memory 106 and/or the RAM 110 may further store data related to the configuration and/or operation of the signal-processing device 102, and/or related to the operation of the one or more subroutines 132. For example, the data may be data gathered by the imaging device 116, data determined and/or calculated by the processor 108, etc. In addition to the controller 104, the signal-processing device 102 may include other hardware resources. The signal-processing device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input.

It may be advantageous for the signal-processing device 102 to communicate with a medical treatment device, medical data records storage device, or network (not shown) through any of a number of known networking devices and techniques (e.g., through a commuter network such as a hospital or clinic intranet, the Internet, etc.). For example, the signal-processing device may be connected to a medical records database, hospital management processing system, healthcare professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

The system 100 may be implemented as computer-readable instructions stored on a single dedicated machine, for example, one with one or more computer processing units. In some examples, the dedicated machine performs only the functions described in the processes of FIG. 2, and any other functions needed to perform those processes. The dedicated machine may be a standalone machine or embedded within another computing machine, such as system 100. In other examples, the functions described in FIG. 2 are integrated within an existing computing machine, such as the machine 100.

In some examples, one or more of the functions of the system 100 may be performed remotely, including, for example, on a server connected to a medical imaging device (such as system 100), through a wired or wireless interface and network. Such distributed processing may include having all or a portion of the processing of system 100 performed on a remote server. In some embodiments, the techniques herein may be implemented as software-as-a-service (SaaS) with the computer-readable instructions to perform the method steps being stored on one or more the computer processing devices and communicating with one or more user devices, including but not limited to system 100.

Further still, the system 100 may include or be connected to a 3D printing system 150 communicatively coupled to the signal processing device 102, through a wireless network 152, for communicating determined VDM results to the 3D printing system for overlaying the VDM results, in a color-coded manner, over a 3D aortic model printed by the 3D printing system.

Several extensions of the VDM processes may be used depending on the applications of use. In some implementations, a high degree of sensitivity to aortic wall deformation may be present, such that errors can be introduced by factors resulting in differing spatial alignment of the two compared aortic geometries. The two areas most susceptible to such error are at the aortic root (sinuses of Valsalva) and at the distal descending aorta at the level of the diaphragm, with the two main contributing factors being cardiac and respiratory motion. The effects of these factors on variation in aortic geometry have been previously described. The aortic root has the highest degree of pulsatory motion of any thoracic aortic segment owing to its close proximity to the heart, with the degree of pulsation amplified during expiration. Additionally, the entire thoracic aorta has a relatively uniform lateral and posterior displacement with expiration. Therefore, the present techniques, in some embodiments, may address such errors, e.g., by relying using uniform displacement correction during image co-registration, especially for those segments of the aorta, like the distal descending aorta, that remain relatively fixed in position by the diaphragm. Separately, non-uniform motion may be analyzed for and compensated for using image processing, when a threshold amount of potential misalignment during image co-registration is determined to exist.

Furthermore, accuracy may be enhanced by acquiring the images during the same phase of respiration (preferably inspiration) and with ECG-gating (preferably in late diastole) in order to minimize errors attributable to the small phasic variations in aortic geometry. In addition to respiratory and pulsation artifacts, "stair-step" artifact is occasionally encountered in ECG-gated CTAs, particularly when studies are performed on scanners with detector rows numbering 64 or less. Stair-step artifact can be problematic as it creates an abrupt shelf-like defect in the 3D aortic segmentation that limits image co-registration. However, modern CT scanners that have been optimized for cardiovascular imaging can greatly minimize the frequency and severity of stair-step artifacts due to increased number of detector rows and decreased gantry rotation time. Implementing the present techniques on such machines, therefore, can further reduce the possible of "stair-step" artifacts.

The techniques may be extended in other ways, as well. For example, while examples herein describe evaluating and diagnosis of dimension changes between measurements taken at the same point in the cardiac cycle, in other examples the present techniques include evaluating and diagnosing (e.g., quantifying) changes in the aortic dimensions between different points in the cardiac cycle (i.e., at differing arterial pressure). The aortic dimensions have been shown to change significantly with pulsation, and measurement of these changes using the present techniques can provide important insights into the elasticity/rigidity of the aortic wall, a characteristic that has been associated with a large variety of cardiovascular diseases.

In other examples, the present techniques may be used to quantify enlargement of other pathologies that manifest as progressive vascular enlargement, including, by way of example, pathologies such as abdominal aortic aneurysm, cerebral aneurysm, iliac artery aneurysm, pulmonary artery enlargement related to pulmonary hypertension, and endoleak after endovascular aortic repair.

Figure 10:
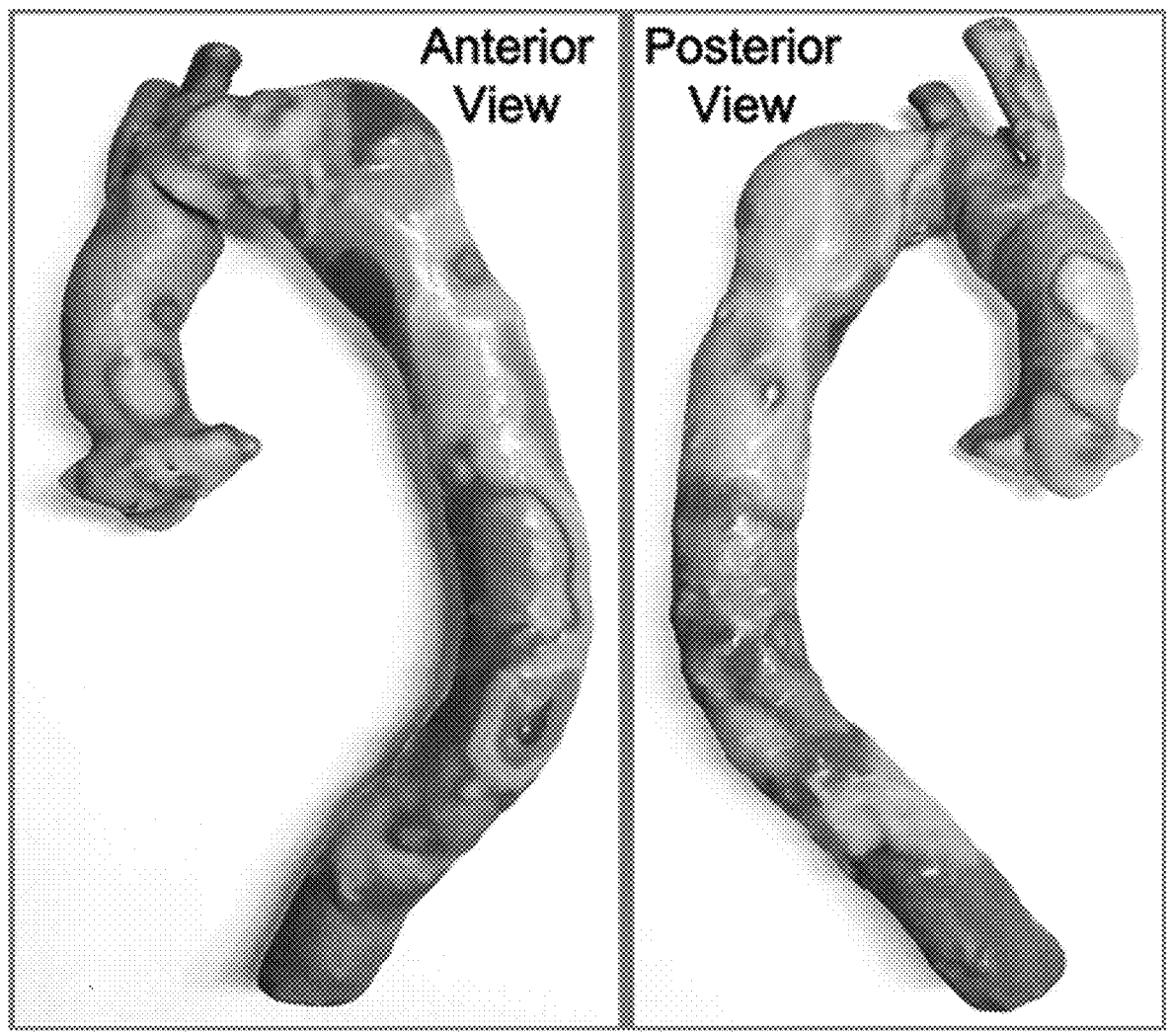
FIG. 10 illustrates a color 3D-printed model of the thoracic aorta produced from the VDM results of a patient with progressively enlarging descending aortic aneurysm presented in FIG. 4, Interval 2. The superimposition of pathophysiologic VDM data on a 3D-anatomic model represents a novel application of medical 3D-printing and may be valuable in operative planning.

The present techniques may also be integrated with 3D printing systems. For example, the data resulting from the VDM techniques herein may be used to superimpose VDM results on full-scale, color 3D printed aortic models, to provide further diagnostic illustration of the resulting aortic pathology analysis. In an example, the VDM results from FIG. 4 (Interval 2) were provided to a 3D color printer and used for color 3D printing of aortic models, with the results shown in FIG. 10. The result is a superimposes imaging-based measurement of pathophysiology, such as aneurysm enlargement, on 3D printed anatomic models, with color-based indications of areas of concern. As demonstrated, the addition of VDM results superimposed on the 3D model surface significantly increases the amount of information that a model contains and, in particular, results in creating patient-specific 3D models. While a computerized VDM provides a detailed overview of the aneurysm enlargement, the 3D printed model, which can be handled and closely studied by surgeons, allows for subtle anatomic and functional observations that are not as easily appreciated on a digital frame, and could facilitate patient education during clinic visits.

The present techniques may be used to study aneurysm pathophysiology due to the high degree of sensitivity to changes in aortic dimensions. There has been increased interest in elucidating the cellular pathways involved in remodeling of the vascular wall leading to the formation of aortic aneurysm. Various cellular signaling pathways along with host-immune interactions have been implicated in the pathogenesis of abdominal aortic aneurysms. These factors are, in part, related to the complex underlying cellular processes responsible for the loss of extracellular matrix and wall remodeling. For example, chronic inflammation of the aorta wall has been implicated in activation of matrix metalloproteinases (MMPs) such as MMP-2 and MMP-9, which have been reported to play a role in aortic wall weakening and subsequent abdominal aortic aneurysm formation. Furthermore, transforming growth factor β (TGF-β) signaling alterations have been widely associated with vascular smooth muscle disease with the genetic basis now identified to involve three distinct pathomechanisms which include perturbation of the TGF-β signaling pathway, disruption of the vascular smooth muscle cell (VSMC) contractile apparatus, and impairment of extracellular matrix synthesis. Advances in our understanding of the underlying pathogenetic alterations involved in the pathogenesis of thoracic aortic disease are providing significant new opportunities for therapeutic interventions using novel pharmaceutical approaches. In this regard, the present techniques may be used to develop validated imaging biomarkers, which would allow for longitudinal quantification of the effects of drug interventions on modulation of disease progression in both human and animal models. The present techniques may be used to image and analyze biomarkers to facilitate development of therapeutic strategies in both preclinical aneurysm models and for use in clinical translational trials undertaking novel therapeutic strategies.

Further still, the present techniques may be used to investigate (i) associations between the techniques herein (also termed VDM) and patient cardiovascular risk factors, (ii) VDM assessment as a mechanism to reclassify patient risk assessments, and (iii) VDM assessment to predict patient outcomes. Considering that the present techniques can be performed respectively on routine clinical CTA scans, the VDM results can be compared with clinical reports as well as a wide-variety of patient demographic parameters and outcomes such as surgical repair strategy, surgical complication rate, re-operation rates, and the occurrence of aorta-specific adverse events during imaging surveillance. Additionally, since the present techniques allow for assessment of aortic enlargement at specific spatial locations along the aortic wall, growth can be co-localized with pathologic features of the aortic wall that are believed to promote aneurysm development such as atherosclerotic plaque (both calcified and lipid-rich), mural thrombus, intimal hyperplasia or wall thickness. Identifying direct correlations between localized aortic wall pathology and regional wall expansion through the present techniques may well advance our understanding of the underlying pathophysiology that leads to aortic aneurysm, and offer new strategies to predict aortic events, risk stratify patients and monitor the effectiveness of pharmacological therapy.

We have demonstrated techniques of vascular deformation mapping and analysis using a non-rigid image registration based technique to measure changes in the size of the aortic lumen between baseline and follow-up ECG-gated thoracic CTA/MRA examinations in patients with mild aortic dilatation, aortic aneurysm and aortic dissection, and that this technique is capable of quantifying and visually displaying the degree of aortic enlargement in a three-dimensional fashion. Furthermore, we have demonstrated that there are clear discrepancies between the VDM results (of the present techniques) and clinical diameter assessments, with the present techniques appearing more sensitive for detection of changes in aortic dimensions owing to reduced measurement error, although formal quantification of degree of error reduction and the potential clinical impacts of a more sensitive analysis of aortic dimension changes require further investigation. The present techniques for measurement of change in aortic wall dimensions can dramatically improve the accuracy of aortic imaging surveillance, informing clinical decision-making, furthering aortic research questions and shedding light on the natural history of aortic disease.

In example embodiments herein, the Jacobian was used for quantifying temporal change in aortic aneurysms using a quantification of the 3D Jacobian determinant rate directly resulting from the B-spline warping registration. However, the full Jacobian tensor can also be projected onto a vector that is more physiologically relevant, allowing for the extraction of directional components of the spatial Jacobian determinant rate (i.e. along the length of the aorta or in the circumferential direction). This approach may allow for better characterization of the mode of aortic wall failure. Directionality in this case would be sensitive to variations in the segmentation surface due to noise and aortic wall imperfections, so it is proposed to couple this analysis with aortic centerline extraction. The vectors could then be determined based on the centerline instead of the 3D model surface orientation and would likely be more robust and provide a smoother surface intensity map.

Alternative to a Jacobian analysis, finite elements may also be utilized based on an aortic segmentation. For example, aortic segmentation may be used to determine surface vertices, which are then transformed using the optimized transform from the automated image registration. The VDM result would then be calculated directly on the surface using finite element modeling of thin plates. In this example embodiment, the VDM result could be further refined to separate membrane and bending responses, and with the inclusion of aortic wall thickness to determine wall stress. All of these metrics could then be mapped to the 3D segmentation surface for visualization, quantification and 3D printing.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method of quantifying enlargement of anatomic dimensions of a vessel, the method comprising:
    obtaining a first volumetric imaging data for at least a segment of a vessel and determining a first 3-dimentional (3D) segmentation and model of the at least a segment of the vessel;
    obtaining a second volumetric imaging data for the segment of the vessel;
    registering the second volumetric imaging data to the first volumetric imaging data and determining a degree of vessel deformation resulting from the registration;
    calculating a quantitative deformation metric using an optimized non-rigid transformation between the second volumetric imaging data and the first volumetric imaging data; and
    mapping of the quantitative deformation metric to a 3D vessel surface model for display.

2. The method of claim 1, wherein the quantitative deformation metric is a 3D spatial Jacobian determinant.

3. The method of claim 1, wherein the quantitative deformation metric is a directional projection of the full spatial Jacobian matrix.

4. The method of claim 1, wherein the quantitative deformation metric is determined by a normalized difference in triangulated surface area of the 3D vessel surface model.

5. The method of claim 1, wherein registering the second volumetric imaging data to the first volumetric imaging data comprises applying a b-spline warping to one or both of the first 3D model and the second 3D model.

6. The method of claim 1, wherein outputting the degree of change in the at least a segment of the vessel for display comprises generating a 3D model of the at least a segment of the vessel, color coding the generated 3D model to indicate various degrees of change in the vessel dimensions of the at least a segment of the vessel, and displaying the 3D model on a display screen.

7. The method of claim 1, wherein outputting the degree of change in the vessel dimensions at least a segment of the vessel for display to a care professional comprises sending degree of change data for the at least a segment of the vessel to a 3D color printing system for color coding, within the 3D color printing system, a physical 3D model indicating, once printed, various degrees of change in the at least a segment of the vessel.

8. The method of claim 1, wherein the degree of change in the at least a segment of the vessel comprises change in anatomic dimensions of at least a segment of the vessel.

9. An apparatus comprising one or more processors and a computer-readable memory storing non-transient instructions that when executed by the one or more processors cause the apparatus to:
    obtain a first volumetric imaging data for at least a segment of a vessel and determine a first 3-dimentional (3D) segmentation and model of the at least a segment of the vessel;
    obtain a second volumetric imaging data for the segment of the vessel;
    register the second volumetric imaging data to the first volumetric imaging data and determine a degree of deformation of an anatomic dimension of a vessel resulting from the registration;

calculate a quantitative deformation metric using an optimized non-rigid transformation between the second volumetric imaging data and the first volumetric imaging data; and map the quantitative deformation metric to a 3D vessel surface model for display.

10. The apparatus of claim 9, wherein the quantitative deformation metric is a 3D spatial Jacobian determinant.

11. The apparatus of claim 9, wherein the quantitative deformation metric is a directional projection of the full spatial Jacobian matrix.

12. The apparatus of claim 9, wherein the computer-readable memory stores non-transient instructions that when executed by the one or more processors cause the apparatus to:

determine the quantitative deformation metric by determining a normalized difference in triangulated surface area of the 3D vessel surface model.

13. The apparatus of claim 9, wherein the computer-readable memory stores non-transient instructions that when executed by the one or more processors cause the apparatus to:

register the second volumetric imaging data to the first volumetric imaging data by applying a b-spline warping to one or both of the first 3D model and the second 3D model.

14. The apparatus of claim 9, wherein the computer-readable memory stores non-transient instructions that when executed by the one or more processors cause the apparatus to:

output the degree of change in the at least the segment of the vessel for display by generating a 3D model of the at least a segment of the vessel, color coding the generated 3D model to indicate various degrees of change in the vessel dimensions of the at least a segment of the vessel, and displaying the 3D model on a display screen.

15. The apparatus of claim 9, wherein the computer-readable memory stores non-transient instructions that when executed by the one or more processors cause the apparatus to:

output the degree of change in the vessel dimensions of the at least a segment of the vessel for display to a care professional by sending degree of change data for the at least a segment of the vessel to a 3D color printing system for color coding, within the 3D color printing system, a physical 3D model indicating, once printed, various degrees of change in the at least a segment of the vessel.

16. The apparatus of claim 9, wherein the degree of change in the at least a segment of the vessel comprises change in anatomic dimensions of the at least a segment of the vessel.

17. The method of claim 1, wherein the anatomic dimensions of the vessel comprise dimensions indicative of at least one of:

aortic diameter;

luminal area; and vessel segmental volume.

18. A system comprising:

an imaging device for generating volumetric imaging data, one or more processors, and a computer-readable memory storing non-transient instructions that when executed by the one or more processors cause the one or more processors to, obtain a first volumetric imaging data for at least a segment of a vessel and determine a first 3-dimentional (3D) segmentation and model of the at least a segment of the vessel;

obtain a second volumetric imaging data for the segment of the vessel;

register the second volumetric imaging data to the first volumetric imaging data and determine a degree of deformation of an anatomic dimension of a vessel resulting from the registration;

calculate a quantitative deformation metric using an optimized non-rigid transformation between the second volumetric imaging data and the first volumetric imaging data; and map the quantitative deformation metric to a 3D vessel surface model for display.

19. The system of claim 18, wherein the quantitative deformation metric is a 3D spatial Jacobian determinant.

20. The system of claim 18, wherein the computer-readable memory stores non-transient instructions that when executed by the one or more processors cause the one or more processors to:

output the degree of change in the at least the segment of the vessel for display by generating a 3D model of the at least a segment of the vessel, color coding the generated 3D model to indicate various degrees of change in the vessel dimensions of the at least a segment of the vessel, and displaying the 3D model on a display screen.

* * * * *